(12) United States Patent
Gaillard et al.

(10) Patent No.: US 7,357,899 B2
(45) Date of Patent: Apr. 15, 2008

(54) REAGENT ADDITION SYSTEM AND METHOD

(75) Inventors: Patrick Gaillard, Bayville, NY (US); Peter Kurzyna, Albertson, NY (US); Drasko Vukicevic, Oyster Bay, NY (US)

(73) Assignee: Oyster Bay Pump Works, Inc., Hicksville, NY (US)

( * ) Notice: Subject to any disclaimer, the term of this patent is extended or adjusted under 35 U.S.C. 154(b) by 0 days.

(21) Appl. No.: 11/545,215

(22) Filed: Oct. 10, 2006

(65) Prior Publication Data

US 2007/0031294 A1 Feb. 8, 2007

Related U.S. Application Data

(62) Division of application No. 10/132,366, filed on Apr. 25, 2002, now Pat. No. 7,125,520.

(60) Provisional application No. 60/286,388, filed on Apr. 25, 2001.

(51) Int. Cl.
*B01L 3/02* (2006.01)
(52) U.S. Cl. .......... 422/100; 422/99; 422/101; 422/102; 222/283; 222/309; 222/287; 604/155; 73/864.18
(58) Field of Classification Search .......... 422/99–102; 222/135, 283, 309, 287; 73/864.02, 864.13; 604/155
See application file for complete search history.

(56) References Cited

U.S. PATENT DOCUMENTS

| | | | |
|---|---|---|---|
| 3,799,406 A | * | 3/1974 | St. John et al. ............. 222/309 |
| 4,008,003 A | | 2/1977 | Pinkerton |
| 4,941,809 A | | 7/1990 | Pinkerton |
| 5,015,157 A | | 5/1991 | Pinkerton et al. |
| 5,044,889 A | | 9/1991 | Pinkerton |
| 5,080,148 A | * | 1/1992 | Florida ................ 141/266 |
| 5,312,233 A | | 5/1994 | Tanny et al. |
| 5,707,212 A | | 1/1998 | Matthews |
| 5,770,160 A | | 6/1998 | Smith et al. |
| 5,863,187 A | | 1/1999 | Bensley et al. |
| 6,006,800 A | | 12/1999 | Nakano |
| 6,110,427 A | | 8/2000 | Uffenheimer |
| 6,132,686 A | | 10/2000 | Gallup et al. |
| 6,143,252 A | | 11/2000 | Haxo, Jr. et al. |
| 6,374,683 B1 | | 4/2002 | Hunicke-Smith |
| 6,399,024 B1 | | 6/2002 | Bevirt et al. |
| 2001/0005490 A1 | | 6/2001 | Kohrmann et al. |
| 2001/0016358 A1 | | 8/2001 | Osawa et al. |
| 2001/0019701 A1 | | 9/2001 | Braun et al. |
| 2001/0036425 A1 | | 11/2001 | Gazeau et al. |
| 2002/0001544 A1 | | 1/2002 | Hess et al. |
| 2002/0001545 A1 | | 1/2002 | Cronenberg et al. |
| 2002/0104389 A1 | | 8/2002 | Hovey |

\* cited by examiner

*Primary Examiner*—Jill Warden
*Assistant Examiner*—Jyoti Nagpaul
(74) *Attorney, Agent, or Firm*—Hoffman & Baron, LLP

(57) ABSTRACT

A piston coupling for a micro-liter range liquid dispensing system for connecting a piston to a piston drive shaft generally includes a U-shaped body portion having a U-shaped arm and an annular barrel-shaped bearing seated in the U-shaped body portion and retained by the U-shaped arm. The bearing includes an axial bore for receiving the piston, wherein the annular barrel-shaped bearing is designed for balancing the forces applied to the piston by the piston drive shaft symmetrically about the centerline of the piston.

4 Claims, 10 Drawing Sheets

REAGENT ADDITION SYSTEM AND METHOD

CROSS-REFERENCE TO RELATED APPLICATIONS

This application is a divisional of U.S. application Ser. No. 10/132,366, filed on Apr. 25, 2002, now U.S. Pat. No. 7,125,520 which claims the benefit of U.S. Provisional Application No. 60/286,388, filed on Apr. 25, 2001.

FIELD OF THE INVENTION

The present invention relates to the dispensing of liquids in the micro-liter range and below and more particularly to a system and method for transferring liquids at accurately controlled rates and volume through the use of independent precision rotary and linear motion mechanisms.

BACKGROUND OF THE INVENTION

Precision liquid dispensing systems have been successfully employed in many applications where safe and accurate handling of fluids is required. Precision liquid delivery is an important function in the production and research of many products, especially for the medical and pharmaceutical industries. Ease of use and reliability, combined with accuracy, are extremely important in the successful performance of each application.

There are several main technologies which are commonly used in dispensing fluids in the micro-liter range. These include piston pumps, peristaltic pumps, time pressure systems, diaphragm pumps and gear pumps. Each of these technologies must incorporate some sort of valving technology along with a method for displacing fluid. It is generally understood that, in order to achieve accurate and reliable dispenses, positive displacement mechanisms have exhibited the best performance. Most positive displacement mechanisms incorporate out of phase check valves and a piston or other positive displacement mechanism to create suction and discharge.

Rotary reciprocating pumps are also commonly used in the industry in order to accomplish small volume dispensing. Rotary reciprocating pumps utilize synchronous rotation and reciprocation of a piston in a precisely mated cylinder bore. One pressure and one suction stroke are completed per cycle. A duct on the piston connects a pair of cylinder ports alternatively with the pumping chamber, i.e., one port on the pressure portion of the pumping cycle and the other on the suction cycle. A pump head module containing the piston and cylinder is mounted in a manner that permits it to be swiveled angularly with respect to the rotation drive member. The degree of angle controls stroke length and in turn flow rate. The direction of the angle controls flow direction. This type of pump has been found to perform accurate transfers of both gaseous and liquid fluids. A typical rotary reciprocating pump is shown in U.S. Pat. No. 4,008,003 to Pinkerton.

A variation of the conventional rotary reciprocating pump is disclosed in U.S. Pat. No. 5,312,233 to Tanny et al. Tanny et al. disclose a rotary/reciprocating liquid dispensing pump having a piston selectively positioned in alignment with one of a plurality of circumferentially spaced small diameter radial passages of a pump housing. Rotation of the piston is achieved conventionally by a stepping motor. However, the rotary motion of the piston is achieved by an electromagnetic clutch/braking mechanism concentrically surrounding a lead screw. The stepping motor is incrementally pulsed and the electromagnetic clutch/braking mechanism energized for selective incremental rotation of the lead screw.

The metering pumps of the prior art suffer from several disadvantages. One disadvantage of the prior art metering pumps is that the rotational and the linear motion of the piston are tied together. In other words, it is not possible with the prior art pumps to independently control the speed of rotational and linear motion of the piston. This has the effect of limiting the accuracy of dispensed liquid volume that can be achieved. In some applications, where it is necessary to provide extremely precise flow rates from inflow and/or outflow ports, it is possible to carefully adjust the angular orientation of a rotary reciprocating pump head module to achieve the desired accuracy. However, this is a difficult hit-or-miss, trial by error procedure that is very time consuming.

Another problem with some prior art dispensing systems is that, once the desired volume of liquid has been dispensed, there is typically some remnant liquid left on the nozzle tip that can sometimes inadvertently drip. In order to prevent excess liquid from dripping from the nozzle, some prior art systems utilize a secondary valve, such as a solenoid valve or a diaphragm valve, to draw back any remnant fluid back into the nozzle. However, a problem with these secondary valves is the added cost and complexity to the system. Additionally, a secondary valve can further add to maintenance, leakage and air bubble problems. Air bubbles in the system obviously decreases accuracy in the dispensed liquid volume.

Additionally, in some applications where, for example, a suspension is to be pumped, it is often desirable to continuously agitate the suspension. This is conventionally accomplished through shaking or stirring means. Again, providing a system with a means to shake or stir liquid during idle dispensing periods not only adds cost and complexity to the system, but can also have detrimental effects such as the introduction of air bubbles to the system. Furthermore, such conventional systems only provide mixing in the external reservoirs and do not provide for mixing within the fluid path.

Finally, conventional system designs are typically large because they do not include multiple pistons in a single housing. As a result, longer and more complex tubing runs are typically provided. When delivering small volumes of liquid, it is desirable to minimize the total fluid path and priming volumes.

Accordingly, it would be desirable to provide a system that addresses these drawbacks of the prior art metering pumps. In particular, it would be desirable to separate control of the rotational and linear motions of the pump piston so that any sequencing of piston rotation and linear movement can be achieved. By separating control of rotary and linear piston motions, increased dosage volume accuracies can be accomplished and any variety of operating methods appropriate for different fluid properties can be implemented.

SUMMARY OF THE INVENTION

The present invention is a system and method for transferring micro-amounts of liquids at accurately controlled rates and volume through the use of independent precision rotary and linear motion mechanisms. The system generally includes a pump module, an indexing module for incrementally translating at least one nozzle mounted thereto and a programmable controller for controlling the pump module and the indexing module.

The pump module generally includes a chambered block, a piston drive assembly having a piston, a first motor mechanically coupled to the piston drive assembly for rotating the piston and a second motor mechanically coupled to the piston drive assembly for axially translating the piston. The chambered block has a liquid chamber, an inlet port in fluid communication with the liquid chamber and a discharge port in fluid communication with the liquid chamber. The inlet port of the chambered block is radially spaced from the discharge port. The piston is rotatably and translationally supported in the liquid chamber of the chambered block and includes a relieved portion. The first motor rotates the piston between a first position wherein the relieved portion of the piston is aligned with the inlet port of the chambered block and a second position wherein the relieved portion of the piston is aligned with the discharge port of the chambered block. The second motor axially translates the piston within the liquid chamber of the chambered block independent of the first motor to alternately draw in and discharge liquid to and from the liquid chamber.

In a preferred embodiment, the piston drive assembly further includes a drive shaft having opposed ends and a drive shaft coupling. The piston is connected and axially aligned with one end of the drive shaft and the drive shaft coupling is connected with the opposite end of the drive shaft. The drive shaft coupling is rotatable together with the drive shaft, but permits axial translation of the drive shaft with respect to the coupling. The first motor is mechanically connected to the coupling and the second motor is mechanically connected to the drive shaft.

Preferably, the pump module further includes a translating block connected to the drive shaft of the piston drive assembly and a lead screw coupled to the second motor and rotatably connected to the translating block. The translating block permits rotation of the drive shaft with respect to the block, but axially translates the drive shaft as the lead screw rotates within the translating block.

In a preferred embodiment, the translating block is connected to the piston drive assembly to permit axial translation of the piston with respect to the translating block. The pump module further includes a spring connected between the piston and the translating block for providing a biasing force against the axial translation of the piston with respect to the translating block.

One way of permitting axial translation of the piston with respect to the translating block is to fix the piston to the drive shaft and permit the drive shaft to axially translate with respect to the translating block. The piston drive assembly is provided with a piston coupling connected between the piston and the drive shaft to fix the piston to the drive shaft. The spring is disposed around the said drive shaft and captured between the piston coupling and the translating block. Thus, when the translating block moves, the force of the spring causes the piston coupling to move.

Alternatively, the translating block is axially fixed to the piston drive shaft and the piston drive assembly includes a piston coupling connected between the piston and the drive shaft that permits axial translation of the piston with respect to the drive shaft. Again, the spring is disposed around the drive shaft and captured between the piston coupling and the translating block to bias the axial translation of the piston.

In still another alternative embodiment, the drive shaft of the piston drive assembly includes an axial bore having a bottom wall and the piston is disposed in the axial bore to permit axial translation of the piston with respect to the drive shaft. The spring is captured within the bore between the piston and the bottom wall. In this embodiment, the translating block is axially fixed to the drive shaft.

In yet another alternative embodiment, the piston drive assembly includes a piston coupling connected between the piston and the drive shaft and a spacer disposed around the drive shaft between the piston coupling and the translating block. The piston coupling permits axial translation of the piston with respect to the piston coupling. The drive shaft includes an axial bore and the spring is captured within the bore to provide a biasing force against the axial translation of the piston. The spacer axially fixes the translating block to the drive shaft of the piston drive assembly.

In further preferred embodiments, the relieved portion of the piston is a longitudinal groove. The longitudinal groove includes a bottom wall, a rear wall, two side walls and fully radiussed transition surfaces between all the walls. The chambered block preferably includes a temperature control means disposed therein for regulating the temperature of a liquid in the chambered block. The chambered block further preferably includes a reservoir connected to the inlet port for supplying a liquid to the liquid chamber and a tube connected at one end to the discharge port and having a nozzle connected at an opposite end thereof for dispensing a liquid from the chambered block.

The pump module can include only one piston drive assembly or a plurality of piston drive assemblies. Where more than one piston drive assembly is utilized, the translating block is connected to each drive shaft of the piston drive assemblies for simultaneously axially translating the drive shafts. The first motor is then mechanically linked to each coupling of the piston drive assemblies for simultaneously rotating the drive shafts.

The present invention further includes a piston coupling for a micro-liter range liquid dispensing system for connecting a piston to a piston drive shaft. The piston coupling includes a U-shaped body portion having a U-shaped arm and an annular barrel-shaped bearing seated in the U-shaped body portion and retained by the U-shaped arm. The bearing has an axial bore for receiving the piston and is designed for balancing the forces applied to the piston by the piston drive shaft directly on the centerline of the piston. Preferably, the annular barrel-shaped bearing includes a pin for connecting the piston to the bearing and for connecting the bearing to the U-shaped body portion. The pin extends transversely through the bearing and is sized to be press-fit into the bearing and slip-fit into the U-shaped body portion for easy mounting and removal of the piston to and from the coupling.

The present invention also involves a method for pumping a liquid through a chambered block having a liquid chamber, an inlet port in fluid communication with the liquid chamber and a discharge port in fluid communication with the liquid chamber, wherein the inlet port is radially spaced from the discharge port. The method includes the steps of: rotating a piston within the liquid chamber until a relieved portion of the piston is aligned with the inlet port; axially retracting the piston until a desired volume of liquid is drawn into the liquid chamber from the inlet port; rotating the piston so that the piston closes both the inlet port and the discharge port; applying pressure to the liquid in the liquid chamber with the piston; absorbing the force of the applied pressure with a spring; rotating the piston until the relieved portion of the piston is aligned with the discharge port; and releasing the force absorbed by the spring whereby the spring drives the piston forward into said liquid chamber.

Another method, according to the present invention, for pumping a liquid through a chambered block having a liquid chamber, an inlet port in fluid communication with the liquid chamber and a discharge port in fluid communication with the liquid chamber, wherein the inlet port is radially spaced from the discharge port, includes the steps of: rotating a piston within the liquid chamber until a relieved portion of the piston is aligned with the inlet port; axially retracting the piston until a desired volume of liquid is drawn into the liquid chamber from the inlet port; rotating the piston until the relieved portion of the piston is aligned with the discharge port; axially translating the piston forward into the liquid chamber while the relieved portion is aligned with the discharge port until a desired volume of liquid is discharged from the liquid chamber into the discharge port; and briefly retracting the piston at the end of its forward translation to reverse fluid pressure applied at the discharge port.

The present invention further involves a method for maintaining fluid motion of a liquid being pumped through a chambered block having a liquid chamber, an inlet port in fluid communication with the liquid chamber and a discharge port in fluid communication with the liquid chamber, wherein the inlet port is radially spaced from the discharge port. The method includes the steps of rotating a piston within the liquid chamber until a relieved portion of the piston is aligned with the inlet port and alternately retracting and inserting the piston in the liquid chamber while the relieved portion is aligned with the inlet port to alternately draw in and discharge liquid through the inlet port to maintain fluid motion during idle pumping periods.

Other objects and features of the present invention will become apparent from the following detailed description considered in conjunction with the accompanying drawings. It is to be understood, however, that the drawings are designed as an illustration only and not as a definition of the limits of the invention.

DETAILED DESCRIPTION OF THE PREFERRED EMBODIMENTS

Figure 1:
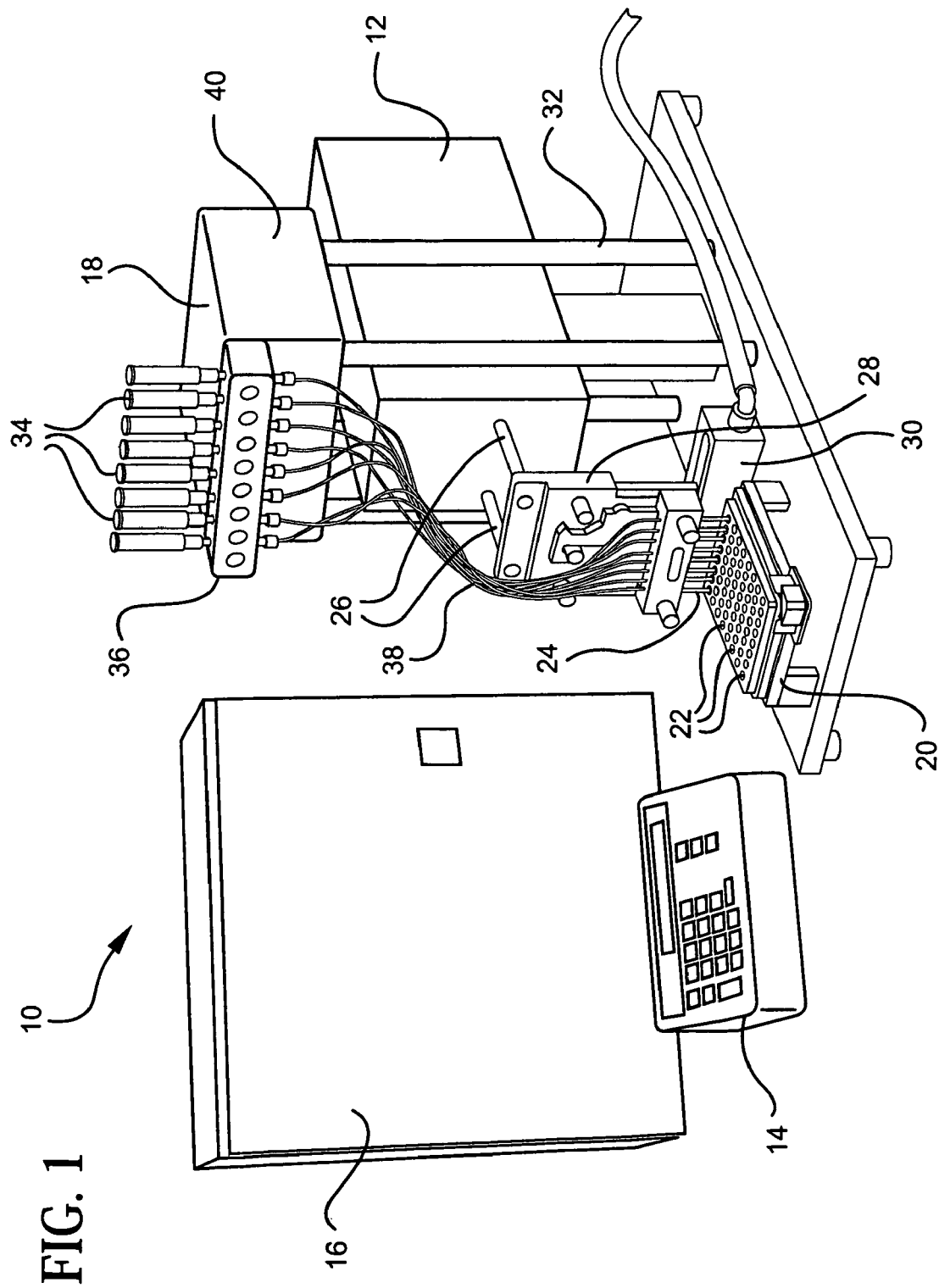
FIG. 1 is a perspective view of the reagent addition system formed in accordance with the present invention.

Referring first to FIG. 1, the system 10 according to the present invention generally includes four component modules: the nozzle indexing module 12; the control interface 14; the control cabinet 16; and the pump module 18.

The nozzle indexing module 12 is the unit on which a plate 20 is placed to be filled. The plate 20 includes a plurality of fluid wells 22 arranged in a series of rows for receiving the dispensed fluid from the system 10. The plate 20 shown in FIG. 1 includes 96 fluid wells 22, however, a variety of well arrays can be addressed with the present invention. The nozzle indexing module 12 is a conventional unit and includes the automated mechanisms (not shown) to step-wise position the nozzles 24 of the pump module 18 over the successive rows of wells 22 of the plate 20. It is available with the motion control features required to fill multi-well plates 20. Typically, the nozzle indexing module 12 includes a stepper motor for incrementally translating one or more pistons 26. The pistons 26 are connected to a mounting plate 28 to which the nozzles 24 of the pump module 18 are mounted. The nozzle indexing module 12 may further include a priming tray 30 for draining fluids. The priming tray 30 is used upon start-up of the system to prime the nozzles 24 and upon completion of the filling procedure to drain any remaining fluid discharged from the system 10.

The control interface 14 is preferably a standard manual keypad which allows operator interface with the system 10. The control interface 14 can also be a PC interface. The control interface 14 is used by the operator to program and control the system 10 and can also be used for manual interruption or adjustment to system operation.

The control interface 14 is in electrical communication with the control cabinet 16, which contains the hardware for operating the system. The control cabinet 16 is typically a stainless steel cabinet placed or mounted near the indexing module 12 and the pump module 18. There are three signal cables (not shown) and one power cable (not shown) coming from the control cabinet 16. One signal cable is electrically connected to the pump module 18, another is connected to the nozzle indexing module 12 and the third is connected to the control interface 14.

The pump module 18, which will be discussed in further detail below, is mounted or otherwise positioned adjacent the nozzle indexing module 12 and the control cabinet 16. The pump module 18 is preferably positioned above the nozzle indexing module 12 and may include legs 32 straddling the indexing module, as shown in FIG. 1. The pump module 18 includes at least one reservoir 34 connected to the pump module in a vertical orientation for supplying a fluid to the pump module. Preferably, the pump module 18 includes a plurality of individual reservoirs 34 arranged in a line, as shown in FIG. 1. For standard 96 and 384 fluid well trays, eight reservoirs 34 work effectively. Each reservoir 34 is connected to a chambered block 36 and is in fluid communication with a respective nozzle 24 via tubing 38. As mentioned above, the nozzles 24 are mounted on the indexing module mounting bracket 28 for translating therewith. Thus, fluid from the reservoirs 34 is pumped through the chambered block 36 and is dispensed through the nozzles 24 into the tray 22.

Figure 2:
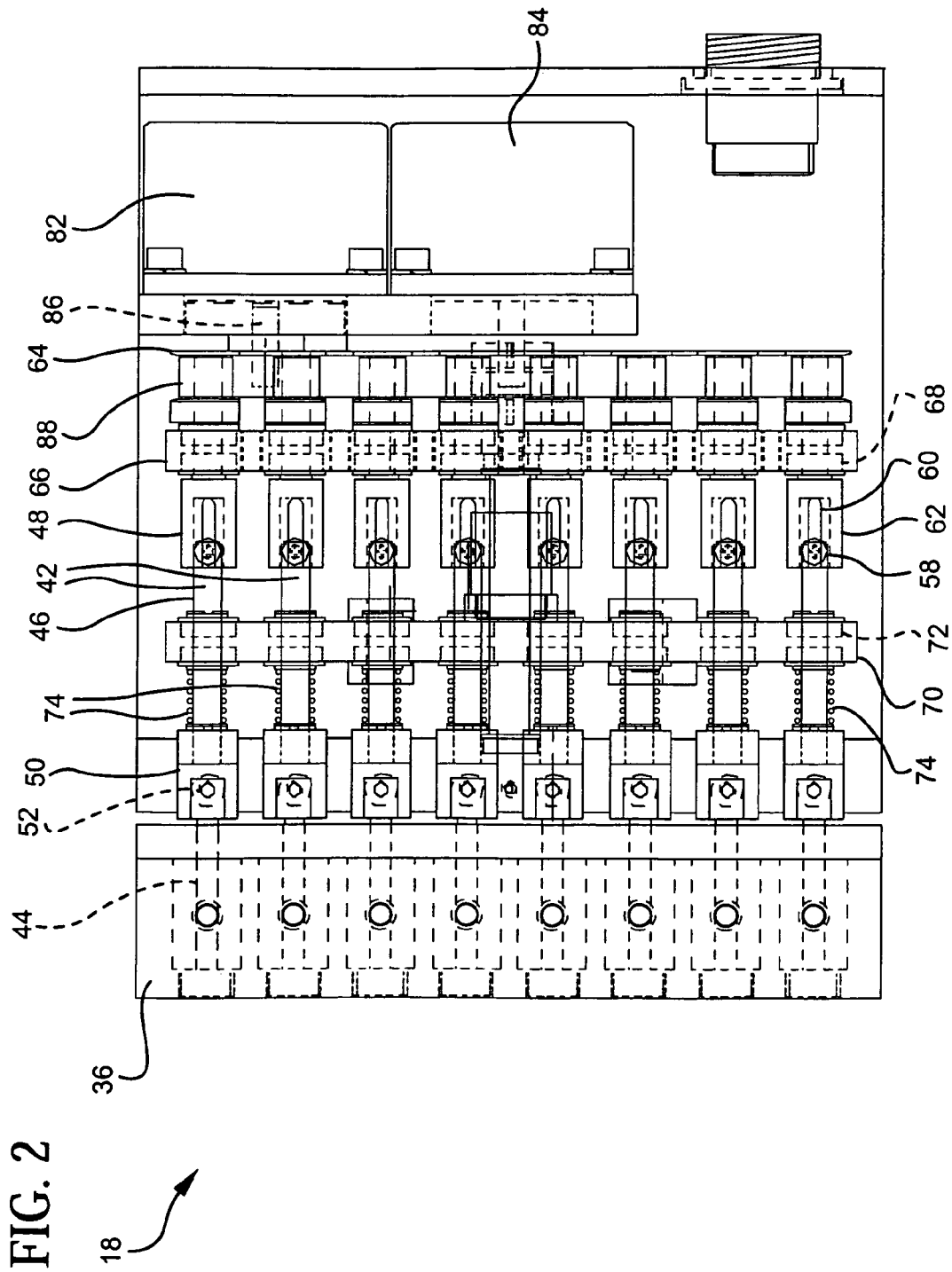
FIG. 2 is a top view of the internal components of the pump module shown in FIG. 1.
Figure 3:
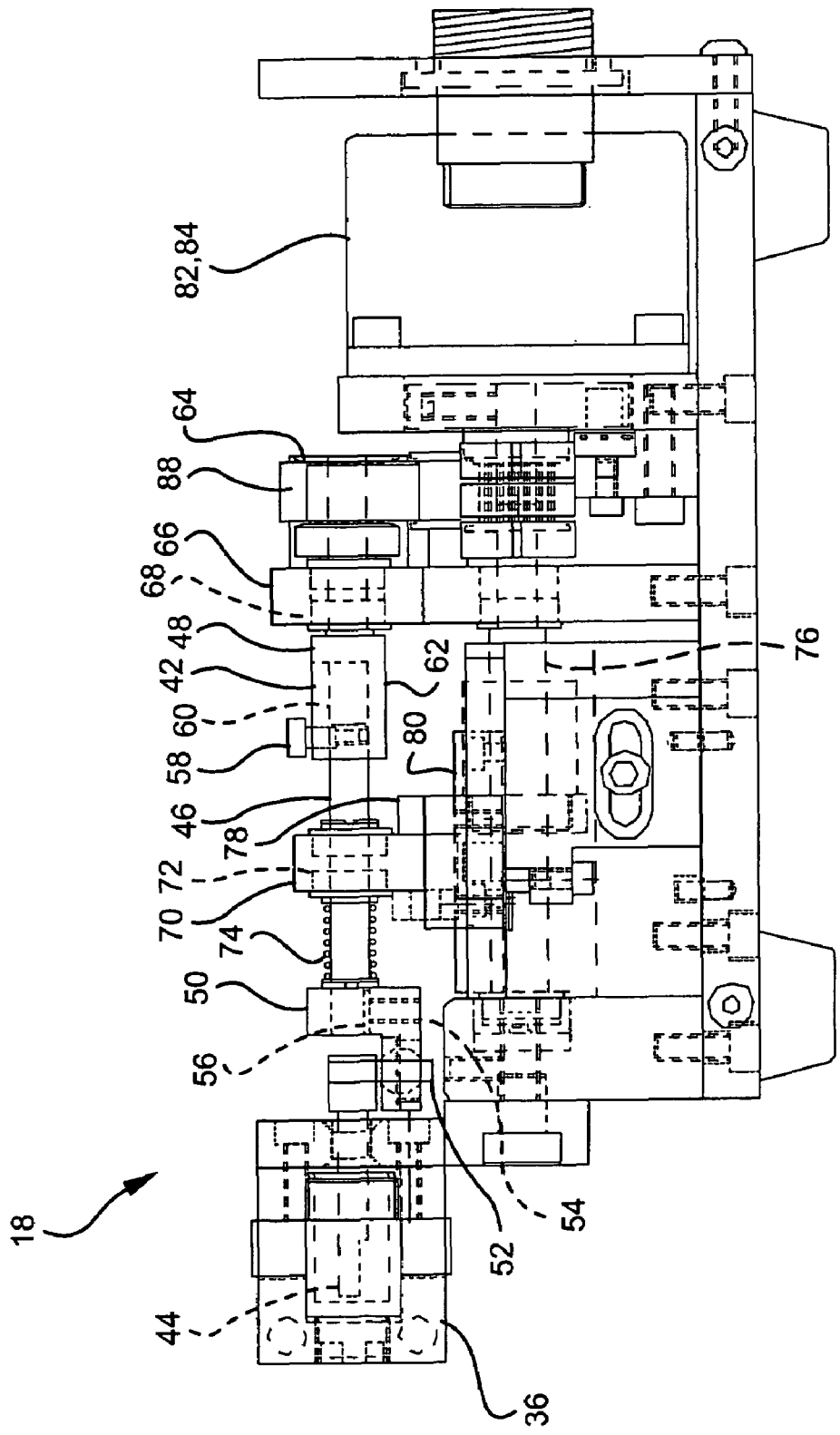
FIG. 3 is a side view of the internal components of the pump module shown in FIG. 1.

Each reservoir 34 is driven by a piston drive assembly 42 contained within a housing 40 of the pump module 18. FIGS. 2 and 3 show top and side elevation views of the internal pump components of the pump module 18 within the housing 40. FIGS. 2 and 3 show eight piston drive assemblies 42 arranged in a side by side relationship, however, the number and arrangement of the piston drive assemblies may vary. Indeed, it is conceivable that the pump module can include only a single piston drive assembly 42, as shown in FIG. 4, with an associated reservoir 34 and nozzle 24.

Figure 4:
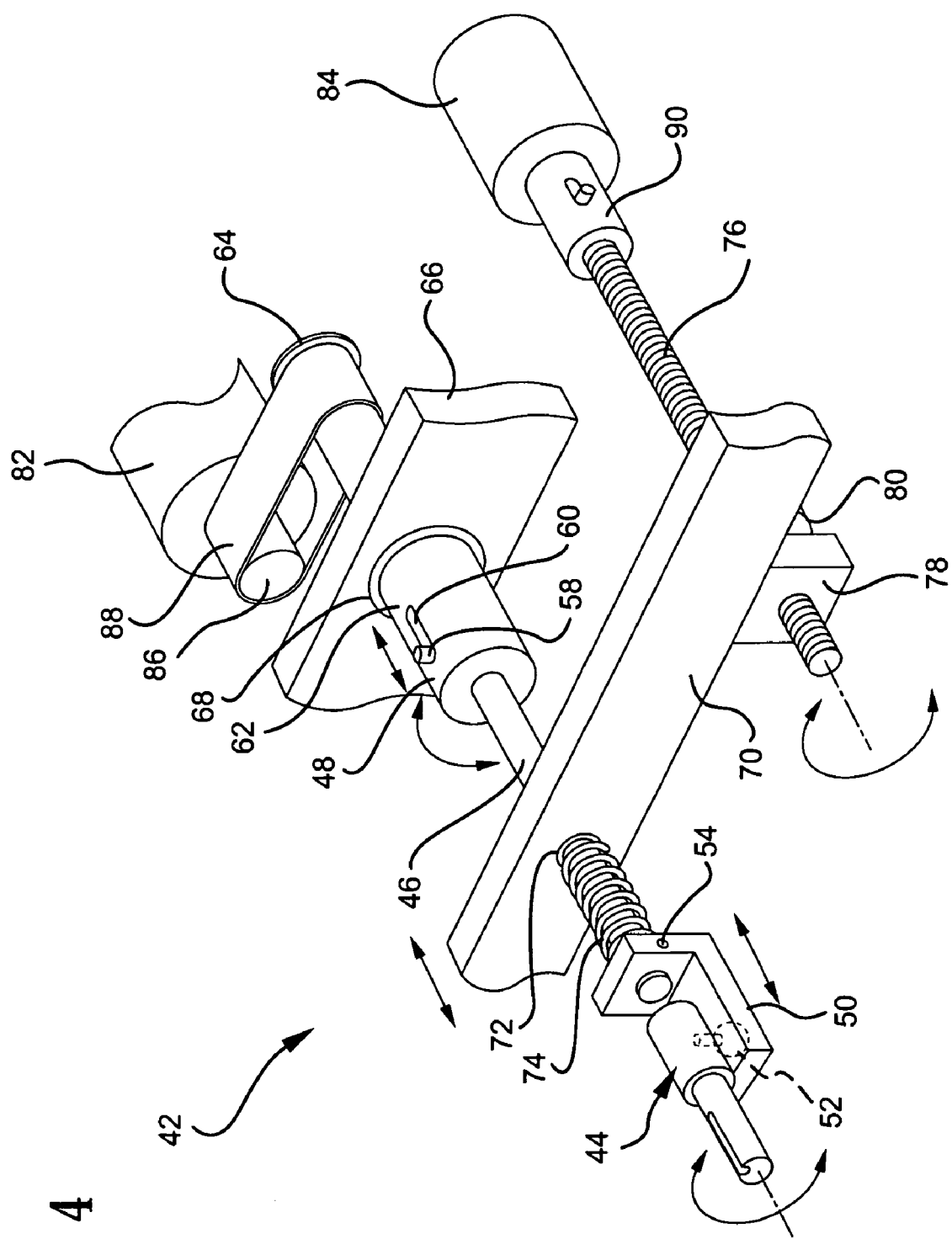
FIG. 4 is a top perspective view of the pump module showing an isolated piston drive assembly.

Referring to FIGS. 2-4, each piston drive assembly 42 generally includes a pump piston 44, a piston drive shaft 46 and a piston drive shaft coupling 48. The pump piston 44 is connected to one end of the piston drive shaft 46 and is axially aligned with the drive shaft. The pump piston 44 can be connected to the drive shaft 46 via a piston coupling 50 in the form of an angled bracket as shown in FIGS. 2-4. One leg of the piston coupling drive bracket 50 is pinned to the pump piston 44 by a pin 52, which may be a pin bearing. The other leg of the piston coupling drive bracket 50 is connected to the piston drive shaft 46 by a pin 54 so that the piston 44 is axially aligned with the drive shaft. The piston coupling 50 enables the use of commercially available metering pump pistons that can easily be connected and disconnected to the piston coupling. Alternatively, the pump piston 44 can be connected directly to the piston drive shaft 46.

At its opposite end, the piston drive shaft 46 is connected to the piston drive shaft coupling 48. This connection is achieved by a pin 58 and slot 60 arrangement whereby the piston drive shaft can axially translate with respect to the coupling. Thus, the piston drive shaft 46 includes a pin 58 that translates in a slot 60 formed in a coupling portion 62 of the coupling 48, or vice versa. The coupling 48 further includes a pulley portion 64 formed on the opposite end of the coupling portion 62. The coupling 48 is rotatably supported in a stationary support block 66 such that the coupling portion 62 extends from one face of the block and the pulley portion 64 extends from the opposite face. The coupling 48 can rotate with respect to the block 66, but is axially fixed to the block by retaining bearings 68.

The drive shaft 46 is further rotatably supported in a translating block 70 connected to the piston drive assembly 42 between the coupling 48 and the piston coupling 50. The translating block 70 includes a drive shaft displacement bearing 72 that permits rotation of the drive shaft with respect to the translating block. The translating block 70 is connected to the piston drive assembly 42 in such a manner that translation of the translating block translates the piston 44. This is most simply achieved by axially fixing the translating block 70 to the piston drive shaft 46. The translating block 70 is further connected to a lead screw 76 for driving the piston drive shaft 46 in an axial direction. The translating block 70 includes a bracket 78 having a lead screw nut 80 through which the lead screw 76 is threaded. Thus, as the lead screw 76 rotates, the lead screw nut 80, along with the translating block 70, travels along the length of the lead screw. Because the translating block 70 is fixed along the axis of the piston drive shaft 46, the piston drive shaft traverses in the axial direction along with the translating block.

Preferably, however, the translating block 70 is connected to the piston drive assembly 42 to permit axial translation of the piston 44 with respect to the translating block. (The purpose of this arrangement will be discussed in further detail below.) Thus, the translating block 70 can be made to permit axial translation of the piston drive shaft 46 therethrough. To axially drive the piston 44, the piston drive assembly 42 includes a spring 74 connected between the piston 44 and the translating block 70 for providing a biasing force against the axial translation of the piston with respect to the translating block. The spring 74 can be captured around the drive shaft 46 between the translating block 70 and the piston coupling 50. The spring 74 provides a biasing force against rearward (i.e., toward the coupling 48) axial translation of the piston coupling 50 with respect to the drive shaft 46. Thus, when the translating block 70 moves, the force of the spring 74 causes the piston 44 to move.

Another way of permitting axial translation of the piston 44 with respect to the translating block 70 is to fix the translating block to the piston drive shaft and make the piston axially translatable with respect to the drive shaft 46. In this embodiment, the drive shaft displacement bearing 72 prevents the drive shaft 46 from axially translating with respect to the translating block 70. The piston coupling 50 is connected to the drive shaft 46 by a pin 54 and slot 56 arrangement, as shown in FIG. 3, whereby the piston coupling, and thus the piston 44, can translate a small distance axially with respect to the drive shaft. The pin 54 can be fixed within the bracket 50 and translate within a slot 56 formed on the drive shaft 46, or vice versa.

Figure 5:
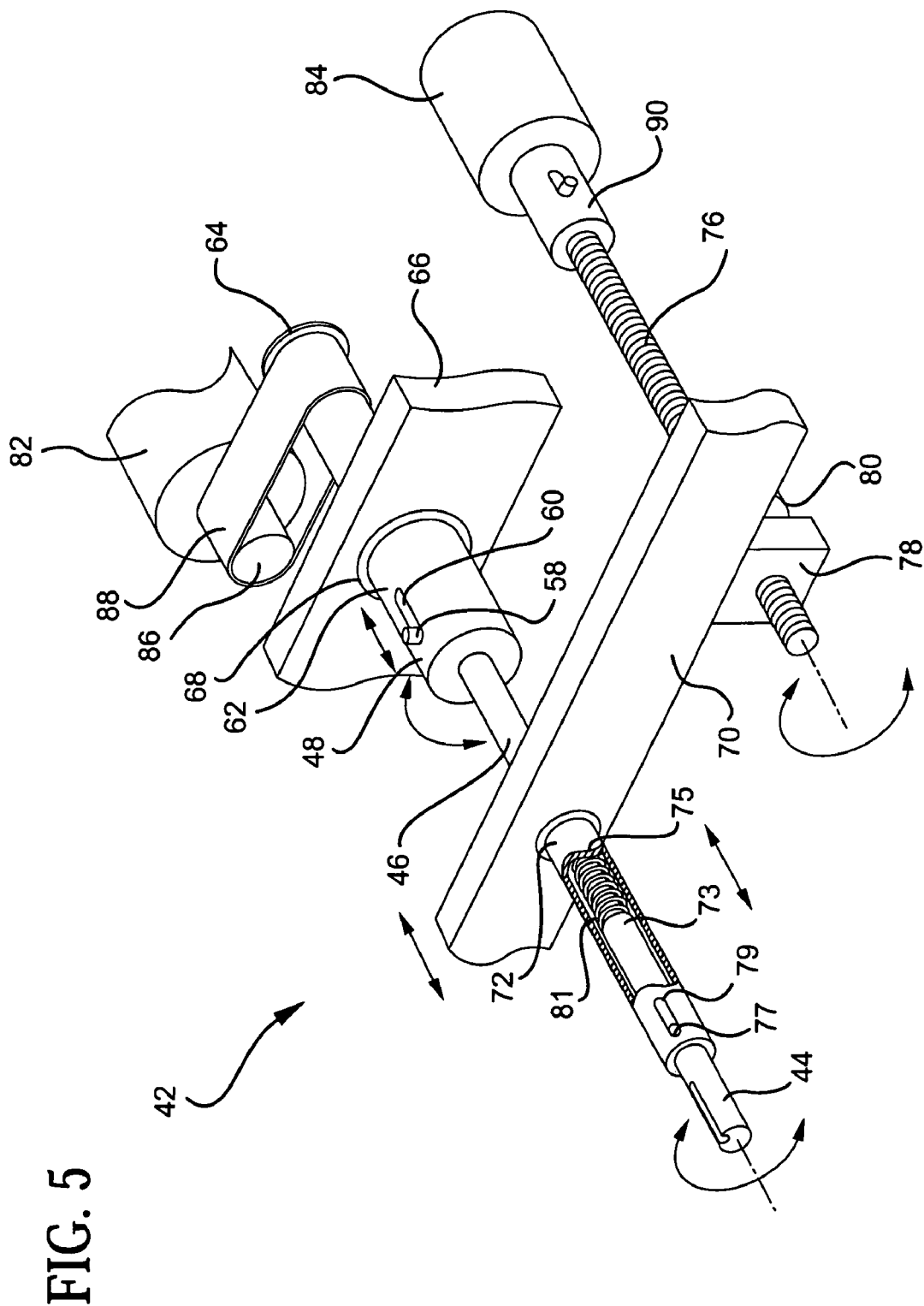
FIG. 5 is a top perspective view of an alternative embodiment of the pump module showing an isolated piston drive assembly.

In still another alternative embodiment, as shown in FIG. 5, the drive shaft 46 of the piston drive assembly 42 includes an axial bore 73 having a bottom wall 75 and the piston 44 is disposed in the axial bore to permit axial translation of the piston with respect to the drive shaft. The piston 44 can include a pin 77 which traverses in a slot 79 formed in the drive shaft 46 to permit axial translation of the piston with respect to the drive shaft. A spring 81 is captured within the bore 73 between the piston 44 and the bottom wall 75. In this embodiment, the translating block 70 is axially fixed to the drive shaft 46, for example by the retaining bearing 72.

Figure 6:
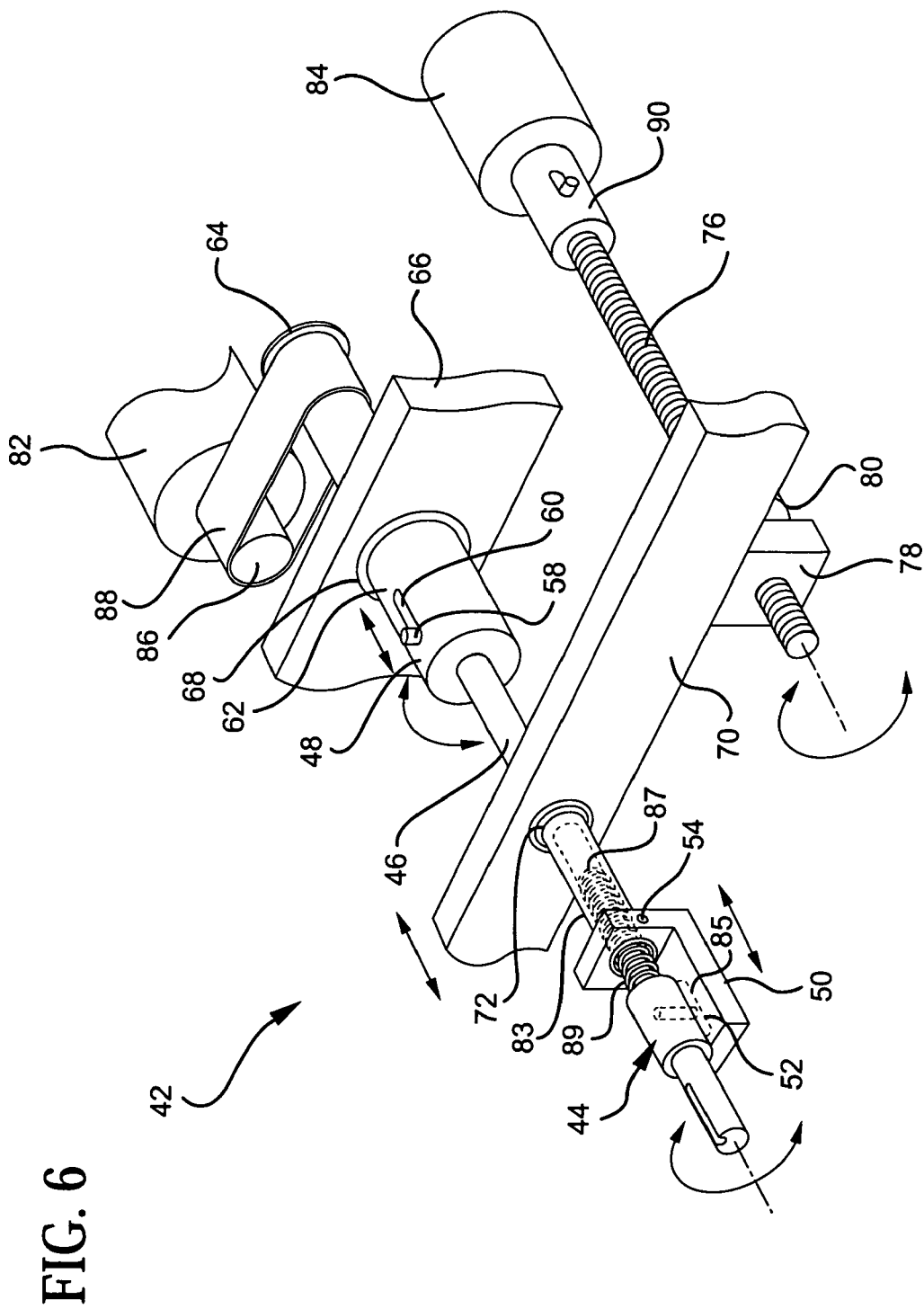
FIG. 6 is a top perspective view of another alternative embodiment of the pump module showing an isolated piston drive assembly.

In yet another alternative embodiment, as shown in FIG. 6, the piston drive assembly 42 includes a piston coupling 50 connected between the piston 44 and the drive shaft 46 and a spacer 83 disposed around the drive shaft between the piston coupling and the translating block 70. The piston coupling 50 permits axial translation of the piston 44 with respect to the piston coupling. This can be achieved by providing a slot 85 in the coupling 50 in which the piston pin 52 translates. The drive shaft 46 includes an axial bore 87 and a spring 89 is captured within the bore to provide a biasing force against the axial translation of the piston 44. The spacer 83 is captured between the piston coupling 50 and the translating block 70 to axially fix the translating block to the drive shaft 46 of the piston drive assembly 42.

Rotation and axial translation of the pump piston 44 are driven by two independent rotary motors 82 and 84. The motors 82 and 84 are also contained within the housing 40 of the pump module 18 along with the piston drive assemblies 42. The motors 82 and 84 are electrically driven, stepping or servo, or pneumatically driven. One motor 82 serves to control rotation of the pump piston(s) 44, while the other motor 84 serves to control linear displacement of the piston(s). The first motor 82 controlling piston rotation is connected on its output shaft 86 to the pulley portion 64 of the piston drive shaft coupling 48. A timing belt 88 connected between the first motor 82 and the coupling 48 is shown in the drawings, however, other mechanical linkages, such as a rack and pinion, can be utilized. Rotation of the coupling 48 in turn rotates the piston drive shaft 46. The second motor 84 controlling linear displacement of the pump piston 44 is coupled to the lead screw 76 by a coupling 90. Rotation of the coupling 90 in turn rotates the lead screw 76. As described above, rotation of the lead screw 76 displaces the lead screw nut 80, which is connected to the translating block 70, which in turn axially translates the pistons 44.

Figure 7:
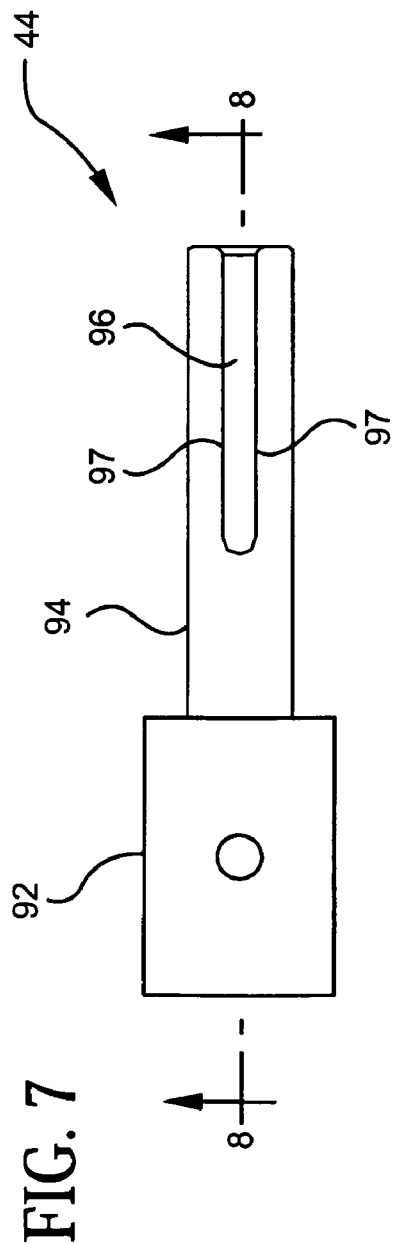
FIG. 7 is a top view of one of the pistons of the piston drive assembly.
Figure 8:
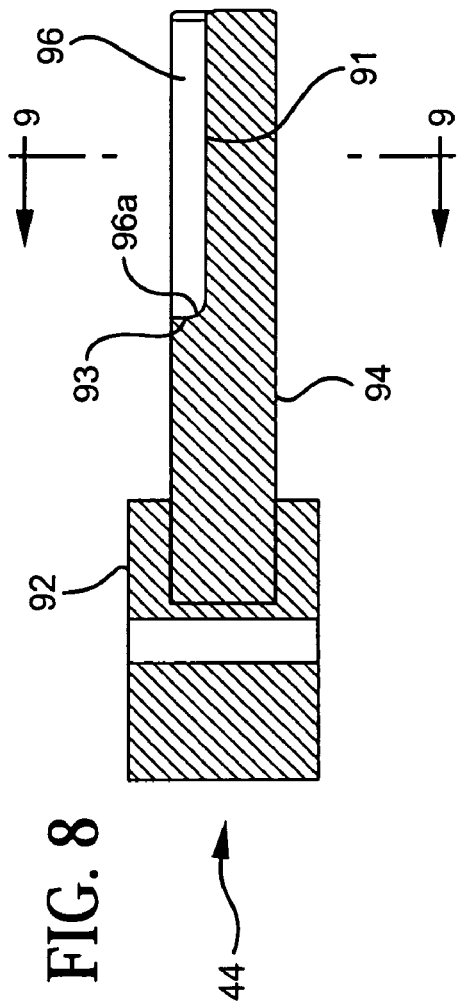
FIG. 8 is a side cross-sectional view of the piston shown in FIG. 7 taken along the line 8-8.
Figure 9:
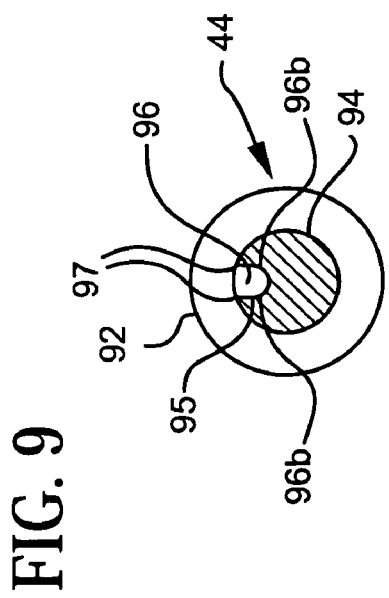
FIG. 9 is an end cross-sectional view of the piston shown in FIG. 8 taken along the line 9-9.

Referring now to FIGS. 7-9, the pump piston 44 is a cylindrical member having a shoulder portion 92, which is secured to the piston coupling 50, and a fluid dispensing portion 94, which is seated in close sliding relationship within the chambered block 36. The fluid dispensing portion 94 is preferably made from a ceramic material and is press-fit or otherwise fixed to and axially aligned with the shoulder portion 92. The fluid dispensing portion 94 of the piston 44 includes a relieved portion 96 designed to direct fluid into and out of the chambered block 36. Preferably, the relieved portion 96 takes the form of a narrow groove formed parallel to the axis of the piston 44. More preferably, the groove 96 includes a fully radiussed transition surface 96a between the bottom 91 and the rear wall 93 of the groove and fully radiussed transition surfaces 96b between the bottom 91 and the side walls 95 of the groove so as to avoid sharp edges within the groove. This minimizes the attachment of air bubbles or fluid components to any surfaces and allows for bubble clearing, which is desirable when transferring micro-amounts of liquid accurately. Additionally, where the groove 96 meets the outer diameter of the piston 44, a sharp edge 97 is preferably provided. In other words, the transition between the groove 96 and the outer surface of the piston 44 is not radiussed, thereby leaving a sharp edge 97 at the transition. The sharp edge 97 is utilized to scrape the inner walls of the liquid chamber 98 of the chambered block 36 as the piston 44 rotates within the chamber to clean the walls during use or during a cleaning cycle. The depth and length of the relieved portion 96 of the piston 44 may be chosen depending on pump size and dose volume range required. Though not preferred, the relieved portion 96 may take other forms, such as a flat.

Figure 10:
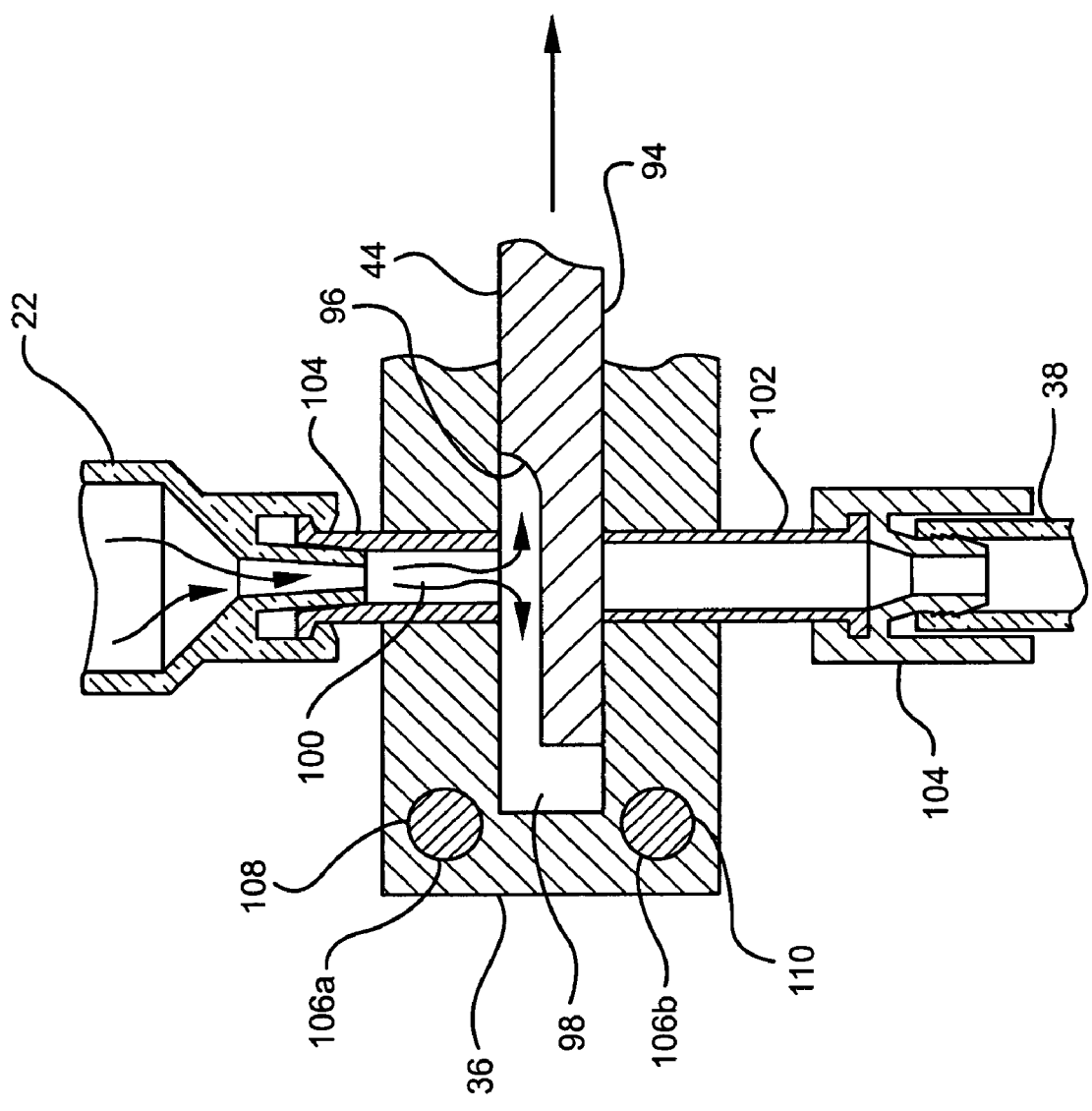
FIG. 10 is a cross-sectional view of the chambered block showing the piston being retracted to intake fluid.
Figure 11:
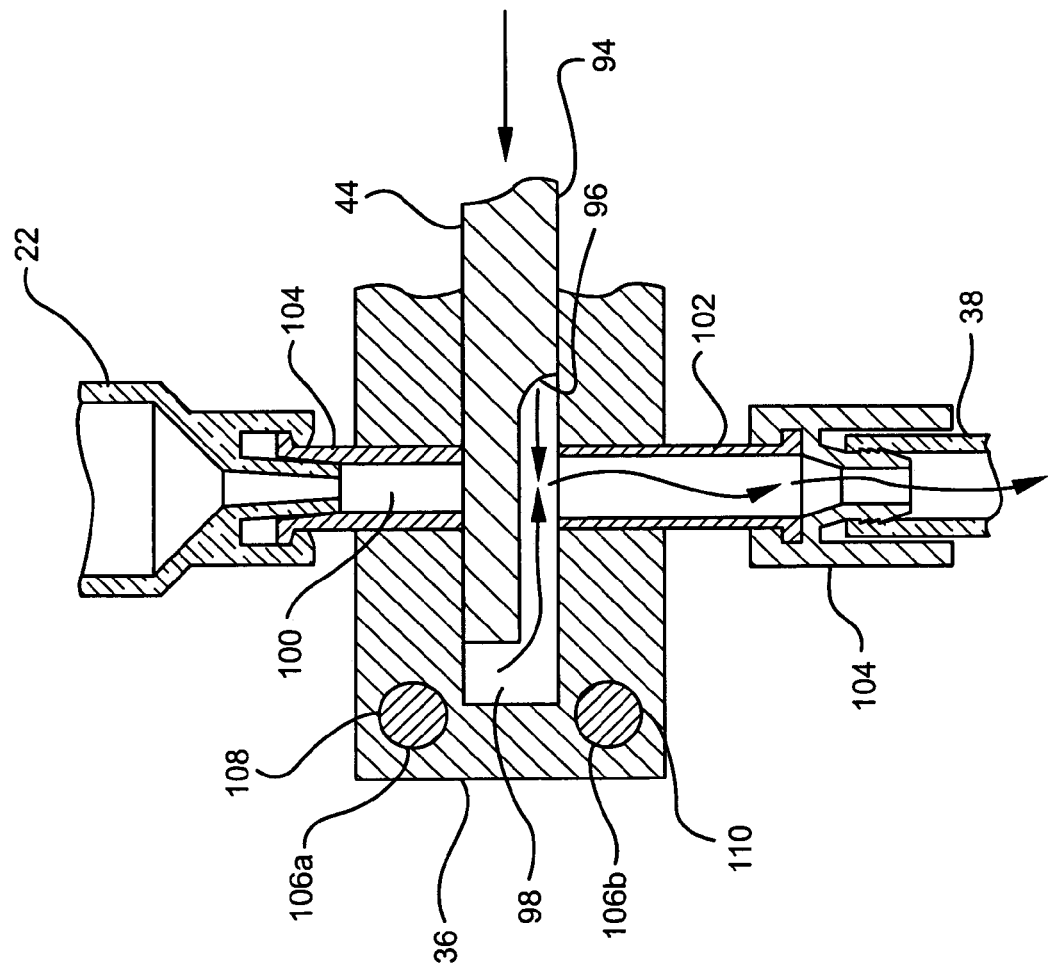
FIG. 11 is a cross-sectional view of the chambered block showing the piston being driven forward to discharge fluid.

FIGS. 10 and 11 illustrate operation of the piston 44 within the chambered block 36. As mentioned above, the fluid dispensing portion 94 of the piston 44 is seated in close sliding relationship within a fluid chamber 98 formed in the chambered block 36. The piston 44 and/or the chambered block 36 may include O-rings (not shown) to ensure a fluid-tight seal therebetween. FIGS. 10 and 11 further show a fluid reservoir 22 connected to an inlet port 100 of the chambered block 36 and tubing 38 connected to a discharge port 102 of the chambered block. The inlet port 100 and the outlet port 102 are radially spaced and are in fluid communication with the fluid chamber 98. In certain applications, only one inlet/outlet port is required. In other applications, a plurality of radially spaced inlet/outlet ports can be provided in the chambered block 36. The reservoir 22 and tubing 38 can be connected to their respective ports by conventional fluid-tight fittings 104. The present invention could also be used to pump fluid from remote reservoirs, wherein intake tubing would be connected to the input port 100 in place of the reservoir 22.

Fluid displacement through the chambered block 36 is achieved by various combinations of rotary and linear motions of the piston 44. In order to draw fluid into the fluid chamber 98 from the reservoir 22, the piston 44 is rotated as required to align the relieved portion 96 with the intake port 100. The piston 44 is then drawn back as required to take in the desired volume of fluid into the chamber 98. Withdrawal of the piston 44 produces a negative pressure within the chamber 98, which draws in fluid from the reservoir 22. The piston 44 is then rotated to align the relieved portion 96 with the discharge port 102 of the chambered block 36. Finally, the piston 44 is driven forward the required distance to force fluid into the discharge port 102 and out of the chambered block 36 via the tubing 38 to produce the desired discharge dose. Again, rotation and translation of the piston 44 is controlled by the individual motors 82 and 84 of the pump module 18.

The chambered block 36 further preferably includes at least one transverse bore 106 formed therein and extending perpendicularly to the fluid chamber 98. The bore 106 can be any shape. A temperature control means 108, 110 is disposed within the bore 106 for regulating the temperature of a liquid flowing through the chambered block 36. The temperature control means can be a conventional cylindrical cartridge type heating element 108 or cooling element 110 that is inserted within the bore 106 to heat or cool the fluid being pumped through the chambered block 36. FIGS. 10 and 11 show a heating element 108 inserted in an upper bore 106a and a cooling element 110 inserted in a lower bore 106b of the chambered block 36. The heating and cooling elements 1108 and 110 can be electrically connected to the control cabinet 16 for heating or cooling the fluid as desired. Alternatively, the temperature control means 108, 110 can take the form of heat exchangers, wherein a heated or cooled liquid is pumped through the bores 106 to transfer or withdraw heat to or from the chamber fluid. This feature provides the ability to control fluid temperature throughout the fluid path.

Figure 12:
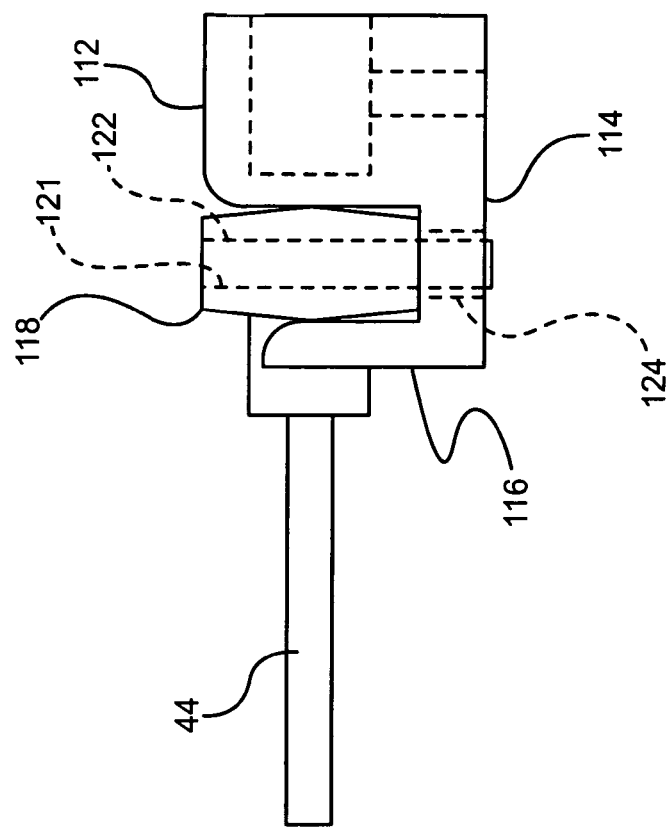
FIG. 12 is a top perspective view of an alternative embodiment of a piston coupling.
Figure 13:
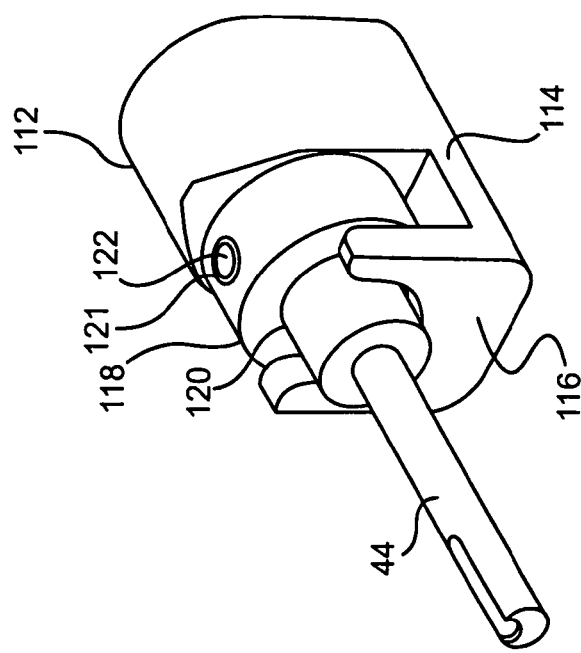
FIG. 13 is a side view of the piston coupling shown in FIG. 12.

FIGS. 12 and 13 show an alternative embodiment of a piston coupling 112 used to connect the piston 44 to the piston drive shaft 46. The piston coupling 112 includes a U-shaped body portion 114 having a U-shaped arm 116. Seated in the U-shaped body portion 114 and retained by the U-shaped arm 116 is an annular barrel-shaped bearing 118. The bearing 118 includes an axial bore 120 for receiving the piston 44. The bearing further includes a bore 121 for receiving a pin 122 for connecting the piston to the bearing. The pin 122 extends transversely through the bearing 118 and is preferably sized to be press-fit into the piston 44 and the bearing 118. The coupling body portion 114 includes a slot 124 for receiving the pin 122 and thereby driving rotation of the piston via the pin. The pin 122 is preferably slip-fit into the slot 124 of the body portion 114. The reason for the slip-fit clearances of the pin 122 is to account for any angular misalignment between the piston drive shaft 46 and the liquid chamber 98 of the chambered block 36. It also provides for simple and effortless mounting and removal of the piston 44 from the coupling 112. The annular barrel-shaped bearing 118 is so designed to balance the forces applied to the piston 44 by the piston drive shaft 46 symmetrically about the centerline of the piston. Prior art coupling designs tend to apply force on the piston in a manner that creates a moment about the piston. This moment can result in stresses on the piston, which in turn can lead to piston failure.

Returning to FIGS. 3-6, an additional feature of the present invention thus far described is the use of spring loaded "lost motion" to enable rapid yet accurate piston displacement so as to increase fluid discharge velocity. "Lost motion" in mechanical devices refers to providing for one portion of a mechanical linkage being in motion while another portion pauses or dwells in one position before resuming motion. In this case, "lost motion" is used to drive the translating block 70 forward while the relieved portion 96 of the pump piston 44 is not aligned with the discharge port 102. Back pressure from the closed discharge port 102 within the fluid chamber 98 will momentarily prevent the piston 44 from moving forward. Because the piston drive assemblies 42 in all the embodiments described above are designed to permit slight axial translation of the piston 44 with respect to the translating block 70, the spring 74, 81 or 89 located between the piston and the translating block absorbs the force applied by the translating block being driven forward. Once the relieved portion 96 of the piston 44 is aligned with the discharge port 102, the spring 74, 81 or 89 drives the piston forward at a high speed to achieve faster discharge of fluid but still the correct metered amount. This rapid delivery enables proper cut off of very small doses from the dispense tips. Alternatively, this effect can be achieved with larger, high torque motors and appropriate drive controls and circuitry.

The above described design separates control of rotary and linear piston motions so as to enable a variety of operating methods appropriate for different fluid properties and dosage volumes. The various methods of operating the two motors 82 and 84 to achieve the above described results are user programmable via the control interface 14 to the control cabinet 16. Alternatively, a PC with dedicated software can be used to interface with the same cabinet.

As a result of the present invention, various advantages are achieved. The system provides alternatives in sequencing rotary and linear piston motions so as to have a single intake for multiple doses. Additionally, the system provides for briefly reversing piston direction at the end of each dose so as to "kick off" drops at dispense tips. In other words, as the piston 44 is driven forward to dispense fluid, as shown in FIG. 11, the translational motor 84 can be programmed to rapidly and briefly reverse direction so that the piston 44 is quickly retracted a short distance. This action of the piston essentially removes any fluid drips from the dispensing nozzles 24. As described above, the system further allows for building pressure in the pump chamber 98 prior to aligning the piston 44 with the discharge port 102 so as to increase fluid velocity and better kick off small fluid droplets. The system additionally allows for keeping fluid in motion during idle periods without dispensing so as to maintain a mixed state of fluid components. This is achieved by aligning the relieved portion 96 of the piston 44 with the intake port 100 and continuously cycling the piston forward and backward within the chambered block chamber 98 until it is time to dispense. The forward and backward action of the piston will alternately draw in fluid from the reservoir 22 and discharge fluid into the reservoir through the intake port 100. The system further provides a very compact arrangement of multiple fluid paths so as to greatly reduce fluid path priming volume and provides for easy maintenance.

For most solutions, dispense volume CV's of 1% or below for doses down to 5 µl and 3% or below down to 1 µl doses can be achieved with the present invention. Indeed, it has been found that doses as low as 0.1 µl are being achieved using this system. Thus, nozzle dispense tip orifices of 0.0015 diameter can be used as compared to prior art diameters of 0.006-0.008. Various pump module designs are conceivable to suit different fill patterns and volume range requirements. They are designed for quick changeover allowing for multiple uses of the same basic system. Piston drive assemblies can be arranged to fill all wells with the same reagent or to put different reagents into specific wells. System speed will depend on how many piston drive assemblies are used.

While there has been described what is presently believed to be the preferred embodiments of the invention, those skilled in the art will realize that various changes and modifications may be made to the invention without departing from the spirit of the invention and it is intended to claim all such changes and modifications as found in the scope of the invention.

What is claimed is:

1. A piston coupling for a micro-liter range liquid dispensing system for connecting a piston to a piston drive shaft, the coupling comprising:
   a U-shaped body portion having a U-shaped arm; and
   an annular barrel-shaped bearing seated in the U-shaped body portion and retained by the U-shaped arm, said bearing including an axial bore for receiving the piston, wherein said annular barrel-shaped bearing is designed for balancing the forces applied to the piston by the piston drive shaft symmetrically about the centerline of the piston, and
   wherein said annular barrel-shaped bearing includes an enlarged mid-section, wherein said bearing is pivotable within said U-shaped body portion for permitting any angular misalignment between the piston drive shaft and the piston.

2. The piston coupling as defined in claim 1, wherein said annular barrel-shaped bearing includes a pin for connecting the piston to said bearing and for connecting said bearing to said U-shaped body portion, said pin extending transversely through said bearing and being sized to be slip-fit into said U-shaped body portion.

3. A piston coupling for a micro-liter range liquid dispensing system for connecting a piston to a piston drive shaft, the coupling comprising:
   a U-shaped body portion having a U-shaped arm; and
   an annular barrel-shaped bearing seated in the U-shaped body portion and retained by the U-shaped arm, said bearing including an axial bore for receiving the piston, wherein said annular barrel-shaped bearing is designed for balancing the forces applied to the piston by the piston drive shaft symmetrically about the centerline of the piston and,
   wherein said U-shaped body portion includes a bore for receiving a piston drive shaft, said body portion bore defining a piston drive shaft axis, and wherein said bearing axial bore defines a piston axis, and wherein said barrel-shaped bearing is pivotable within said U-shaped body portion for permitting angular misalignment between said piston drive shaft axis and said piston axis.

4. The piston coupling as defined in claim 3, wherein said annular barrel-shaped bearing includes a pin for connecting the piston to said bearing and for connecting said bearing to said U-shaped body portion, said pin extending transversely through said bearing and being sized to be slip-fit into said U-shaped body portion.

* * * * *